(12) United States Patent
Norton et al.

(10) Patent No.: US 9,592,061 B2
(45) Date of Patent: Mar. 14, 2017

(54) MODULAR REAMER DRILL TIP CONNECTOR ASSEMBLY

(71) Applicant: Biomet Manufacturing, LLC, Warsaw, IN (US)

(72) Inventors: Daniel Norton, Indianapolis, IN (US); Kevin T Stone, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 120 days.

(21) Appl. No.: 14/019,627

(22) Filed: Sep. 6, 2013

(65) Prior Publication Data
US 2015/0073417 A1    Mar. 12, 2015

(51) Int. Cl.
*A61B 17/00*    (2006.01)
*A61B 17/16*    (2006.01)

(52) U.S. Cl.
CPC ...... *A61B 17/1617* (2013.01); *A61B 17/1675* (2013.01)

(58) Field of Classification Search
None
See application file for complete search history.

(56) References Cited

U.S. PATENT DOCUMENTS

| 8,454,608 | B2 | 6/2013 | Victor et al. | |
| 8,882,413 | B2* | 11/2014 | Hecht | B23B 51/02 408/226 |
| 2003/0097133 | A1* | 5/2003 | Green | A61B 17/1617 606/80 |
| 2003/0219321 | A1* | 11/2003 | Borschert | B23B 51/02 408/230 |
| 2008/0195104 | A1 | 8/2008 | Sidebotham et al. | |
| 2011/0015634 | A1 | 1/2011 | Smith et al. | |

OTHER PUBLICATIONS

"Bixcut IM Reamer System", Stryker Brochure (2009), 8 pages.

* cited by examiner

*Primary Examiner* — Sameh Boles
(74) *Attorney, Agent, or Firm* — Schwegman Lundberg & Woessner, P.A.

(57) ABSTRACT

A reamer assembly, comprising a modular drill tip having a cutting edge proximate a first end, a pair of flexible arms extending from and proximate to a second end and a first through-hole positioned between the first and second ends along a longitudinal axis, wherein the first through-hole is configured to receive a guide wire during a reaming process; and a reamer shaft having a receiving end that is configured to receive and releasably hold in axial alignment thereto the pair of flexible arms, the reamer shaft having a second through-hole that is configured to receive the guide wire during the reaming process, wherein the first and second through-holes together create a common through-hole that is positioned along the longitudinal axis.

12 Claims, 10 Drawing Sheets

MODULAR REAMER DRILL TIP CONNECTOR ASSEMBLY

TECHNICAL FIELD

The present teachings generally relate to orthopedic reamers, and more particularly, to a releasably connectable modular drill tip for an orthopedic reamer.

BACKGROUND OF THE DISCLOSURE

The statements in this section merely provide background information related to the present disclosure and should not be construed as constituting prior art.

Many portions of the human anatomy naturally articulate relative to one another. Generally, the articulation of these anatomic regions is smooth and non-abrasive in nature, particularly in the presence of natural tissues, such as cartilage and strong bone. Over time, however, due to injury, stress, degenerative health problems and various other issues, the ease by which these anatomic regions are able to articulate degenerates in quality, thereby leaving the articulation of these anatomic regions abrasive and unnatural. For example, injury may cause the cartilage or the bony structure to become weak, damaged, or even non-existent. As a result, the natural articulation of these anatomical regions is no longer possible for these affected individuals. At such times, it may be desirable to replace the affected anatomical regions with a prosthetic component or other such biomedical implant device so that normal articulation may be restored.

To replace the affected anatomical region with a prosthetic component or implant device, it may be necessary to cut or remove portions of bone and associated tissue matter with a reaming device (reamer). For instance, in accordance with certain orthopedic procedures, a reamer may be used to cut and bore into the intramedullary space (inner canal) of a long bone such as the femur, tibia or humerus, particularly to clean and create a space for the implant to be received and/or to help mend a fractured bone.

Before the reaming process commences, a wire is typically inserted into the space to serve as a guide for receiving the reamer as it is inserted into the intramedullary space. In some cases, multiple reamers of varying widths are used during the reaming process so that the intramedullary space can be appropriately shaped to sufficiently correspond to the geometry of the implant component being installed. Although conventional reaming systems are somewhat adequate for their intended purposes, these systems can be improved. For instance, when the reaming process requires multiple reamers to be used, conventional systems require that each reamer be extracted from the intramedullary space and slid off the guide wire before the next reamer can be advanced over the guide wire and into the intramedullary space. This process can be time consuming and inconvenient, especially if several reamer interchanges are required.

Many conventional orthopedic reamers are constructed of two parts, a one-piece reamer cutting head and a reamer shaft that connects to the cutting head assembly. The one-piece reamer cutting head is formed from a single block of metal and is machined to include a series of blades or flutes that are designed to remove the bone and tissue as part of the reaming process. As many of these cutting heads are used multiple times before being discarded, the blades require frequent and costly resharpening and sterilization processes. As such, there is a need to provide an improved reamer assembly that addresses one or more of these known deficiencies within the art.

SUMMARY OF THE DISCLOSURE

The present disclosure addresses some of the known deficiencies within the art by providing a modular and disposable reamer drill tip assembly that is releasably connectable to a reamer shaft.

In accordance with one aspect of the present application, a reamer assembly is provided and comprises a modular drill tip having a cutting edge proximate a first end, a pair of flexible arms extending from and proximate to a second end and a first through-hole positioned between the first and second ends along a longitudinal axis, wherein the first through-hole is configured to receive a guide wire during a reaming process. The reamer assembly also comprises a reamer shaft having a receiving end that is configured to receive and releasably hold in axial alignment thereto the pair of flexible arms, wherein the reamer shaft has a second through-hole that is configured to receive the guide wire during the reaming process. Moreover, in accordance with this embodiment, the first and second through-holes together create a common through-hole that is positioned along the longitudinal axis.

In accordance with yet another aspect of the present application, a reamer assembly is provided and comprises a modular drill tip having a cutting edge proximate a first end, a pair of flexible arms extending from a base portion that is positioned proximate to a second end and a first through-hole positioned between the first and second ends along a longitudinal axis, wherein the first through-hole is configured to receive a guide wire during a reaming process; and a reamer shaft having a receiving end that includes a counterbored hole that is configured to receive, and releasably engage in axial alignment thereto, the pair of flexible arms, the reamer shaft having a second through-hole that is configured to receive the guide wire during the reaming process, wherein the first and second through-holes together create a common through-hole that is positioned along the longitudinal axis. In accordance with this aspect of the present application, the engagement between the pair of flexible arms and the counterbored hole is configured to transmit torsional loads that are created when the reamer assembly is subjected to rotary motion to the base portion of the modular drill tip.

In accordance will still another aspect of the present application, a modular drill tip for an orthopedic reamer is provided and comprises a cutting edge proximate a first end, the cutting edge being configured to penetrate a bony structure as the drill tip is imparted with rotary motion; a pair of flexible arms extending from and proximate to a second end, the pair of flexible arms being configured to releasably conform with a receiving end of a reamer shaft; and a through-hole positioned between the first and second ends along a longitudinal axis, the through-hole being configured to receive a guide wire during a reaming process.

Still other objects and benefits of the application will become apparent from the following written description along with the accompanying figures.

BRIEF DESCRIPTION OF THE DRAWINGS

The above-mentioned aspects of the present application and the manner of obtaining them will become more apparent and the teachings of the present application itself will be better understood by reference to the following description of the embodiments of the present application taken in conjunction with the accompanying drawings, wherein.

Corresponding reference characters indicate corresponding parts throughout the several views. Although the exemplification set out herein illustrates embodiments of the present application, in several forms, the embodiments disclosed below are not intended to be exhaustive or to be construed as limiting the scope of the present application to the precise forms disclosed.

DETAILED DESCRIPTION

The embodiments of the present application described below are not intended to be exhaustive or to limit the teachings of the present application to the precise forms disclosed in the following detailed description. Rather, the embodiments are chosen and described so that others skilled in the art may appreciate and understand the principles and practices of the present application.

Unless defined otherwise, all technical and scientific terms used herein have the same meaning as commonly understood by one of ordinary skill in the art to which this application belongs. Although any method and materials similar or equivalent to those described herein can be used in the practice or testing of the present application, the specific methods and materials are now described.

Figure 1:
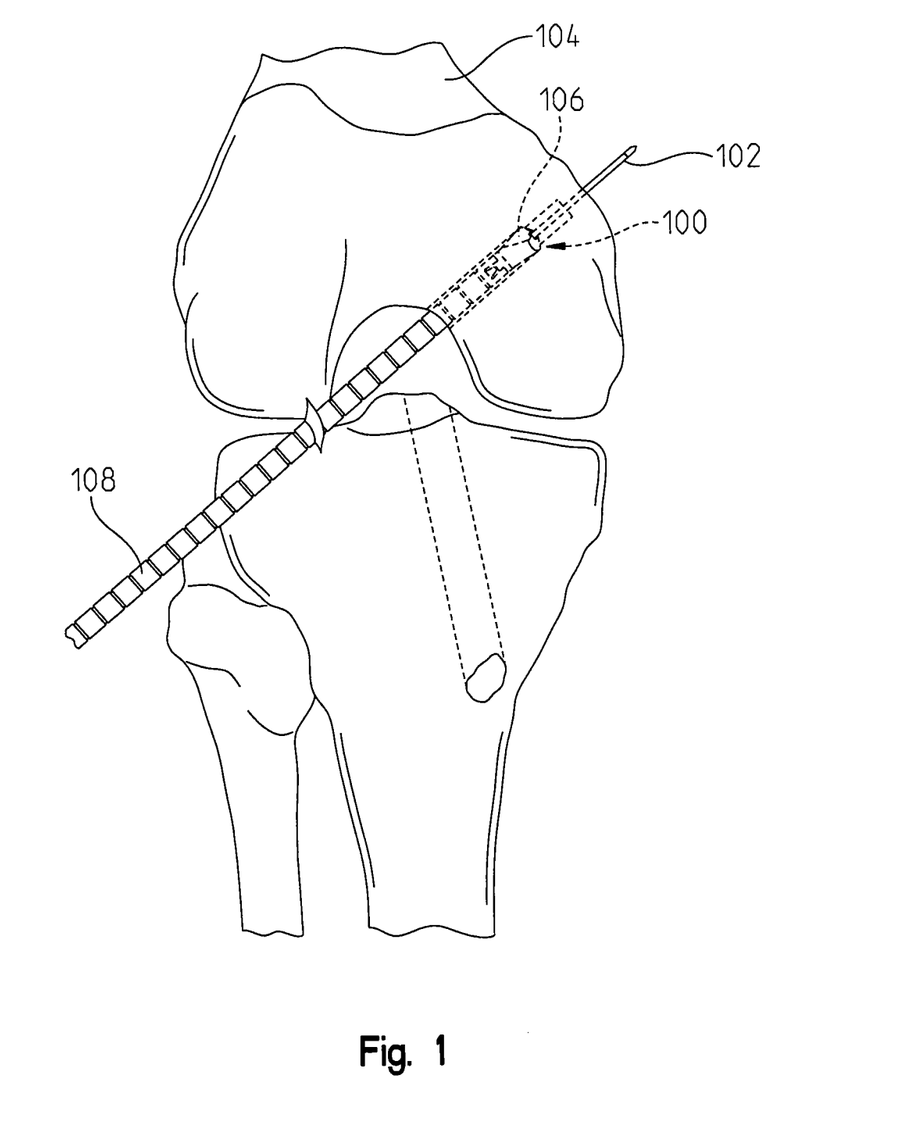
FIG. 1 represents a perspective view of an illustrative modular reamer drill tip connector assembly in accordance with the teachings of the present disclosure and associated with a reamer that has been advanced over a guide wire and is reaming the medial femoral cortex as part of an illustrative surgical procedure.

FIG. 1 depicts a modular reamer drill tip connector assembly associated with a reamer that has been advanced over a guide wire and is reaming the medial femoral cortex as part of an illustrative surgical procedure in accordance with the teachings of the present disclosure. More particularly, in accordance with this illustrative embodiment, a guide wire 102 has been inserted through the lateral portal of a femur 104 and a reamer assembly 100 has been inserted over the guide wire 102 to ream the femoral socket with a modular reamer drill tip connector assembly 106. To cause the drill tip connector assembly 106 to ream the femur 104, the drill tip connector assembly 106 has been coupled to a reamer shaft 108 that in turn is coupled with the chuck of a corresponding orthopedic drill (not shown) that is configured to impart rotary motion to the drill tip connector assembly 106 via the reamer shaft 108.

Further details with respect to the contemplated drill tip connector assemblies of the present teachings can be appreciated from referencing FIGS. 2-11, which are now described in greater detail. It should be understood and appreciated herein that the various drill tip connector assemblies described and illustrated within the present disclosure are intended to establish a frictional relationship with the reamer shafts of which they are releasably coupled to, and particularly such that when the connector assemblies are releasably coupled to the reamer shafts, the drill tip connector assemblies are configured to be held in axial alignment with the reamer shaft as the reamer assembly is advanced over the guide wire.

Figure 2:
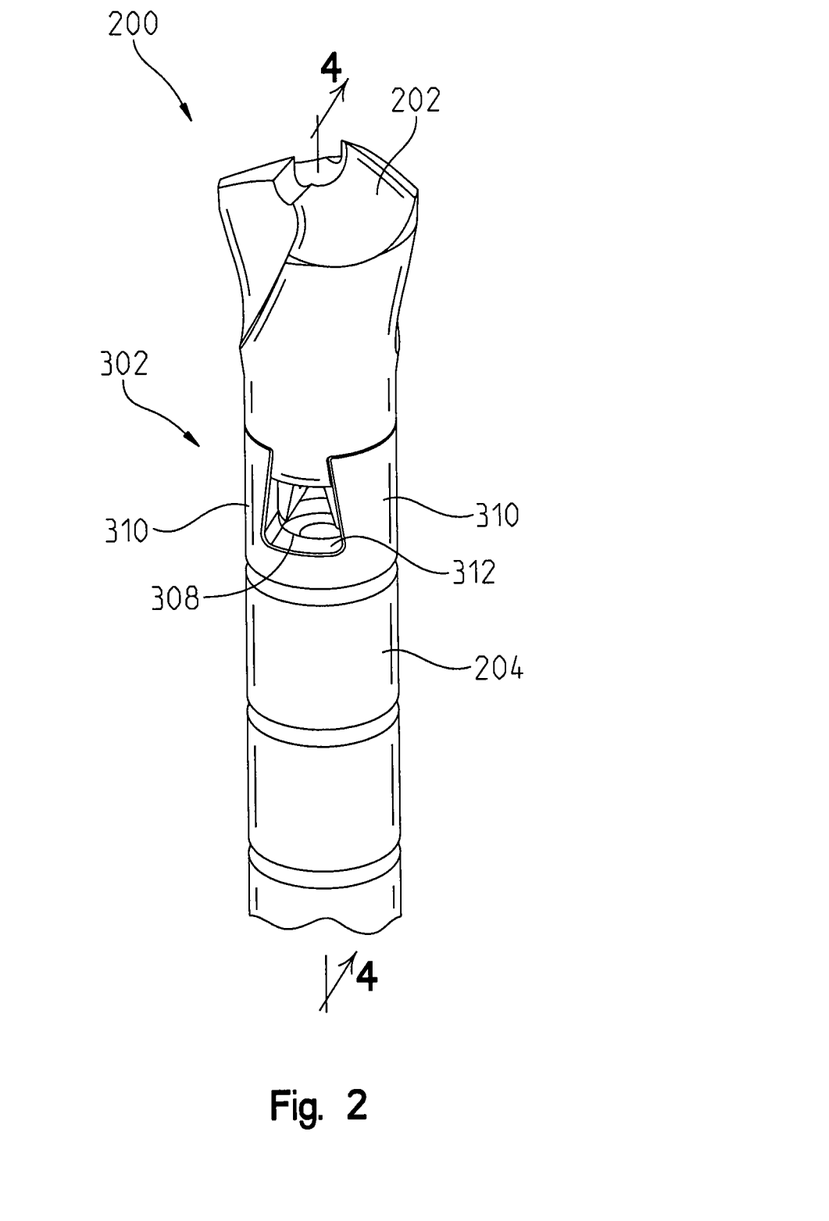
FIG. 2 represents a partial perspective view of an illustrative modular reamer drill tip connector assembly coupled to a reamer shaft in accordance with the teachings of the present disclosure.
Figure 4:
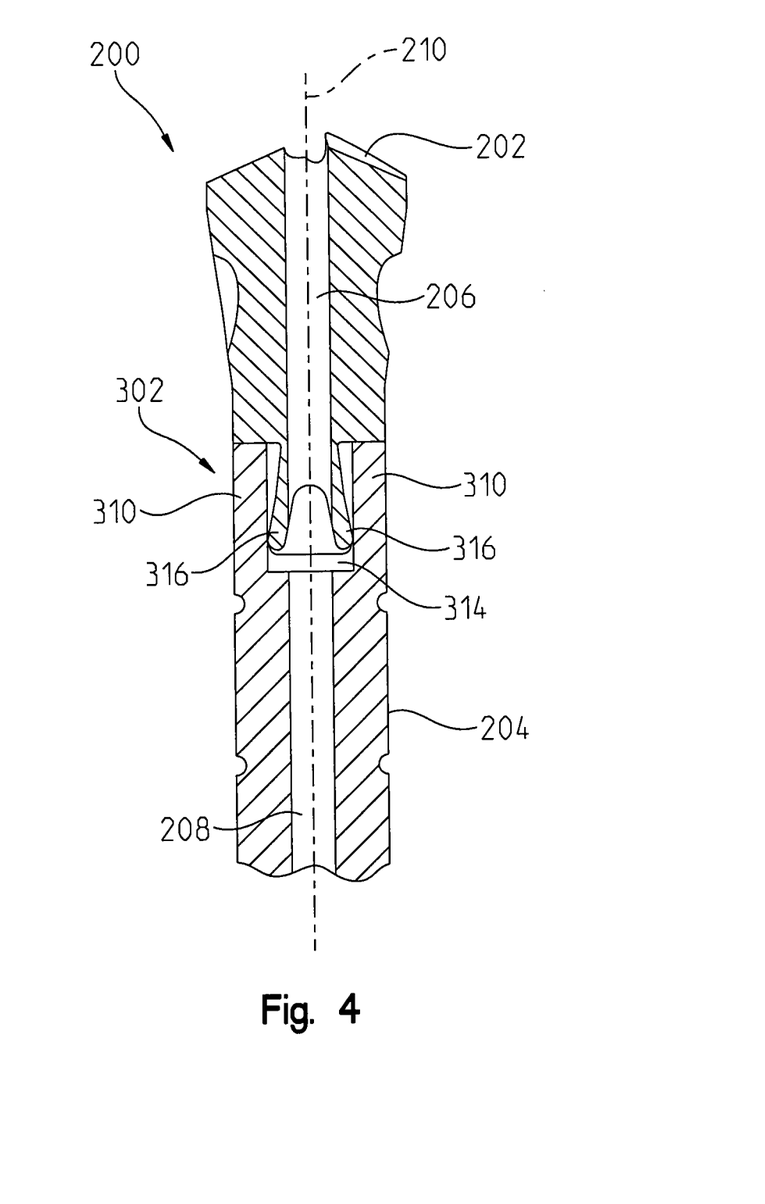
FIG. 4 represents a front, cross-sectional view of the illustrative modular reamer drill tip connector assembly coupled to the reamer shaft and taken along line 4 of FIG. 2.

Moving now to FIG. 2, an illustrative reamer assembly 200 in accordance with an illustrative embodiment of the present disclosure is depicted. The reamer assembly 200 includes a cutting tip 202 that is configured to be removably coupled to a reamer shaft 204 as part of a reaming procedure, such as the reaming procedure shown in FIG. 1, for instance. As shown in this embodiment, when the reamer shaft 204 and the cutting tip 202 are coupled to one another, the cutting tip 202 can be axially aligned with the reamer shaft 204 such that a torsional force from the reamer assembly 200 during a reaming procedure can be transmitted through a solid portion of the cutting tip 202. As shown in FIG. 4, to advance the reamer assembly 200 over a guide wire (such as guide wire 102, shown in FIG. 1), both the cutting tip 202 and the reamer shaft 204 include a through-hole along their respective center axes (i.e., through-hole 206 of the cutting tip 202 and through-hole 208 of the reamer shaft 204). As those of skill in the art will readily understand and appreciate herein, the releasable connection between the cutting tip 202 and the reamer shaft 204 can be configured such that through-holes 206 and 208 are capable of aligning with each other along the center axis 210 of the reamer assembly 200 such that a common through-hole that is adapted to receive the guide wire during a reaming process is created.

Figure 3:
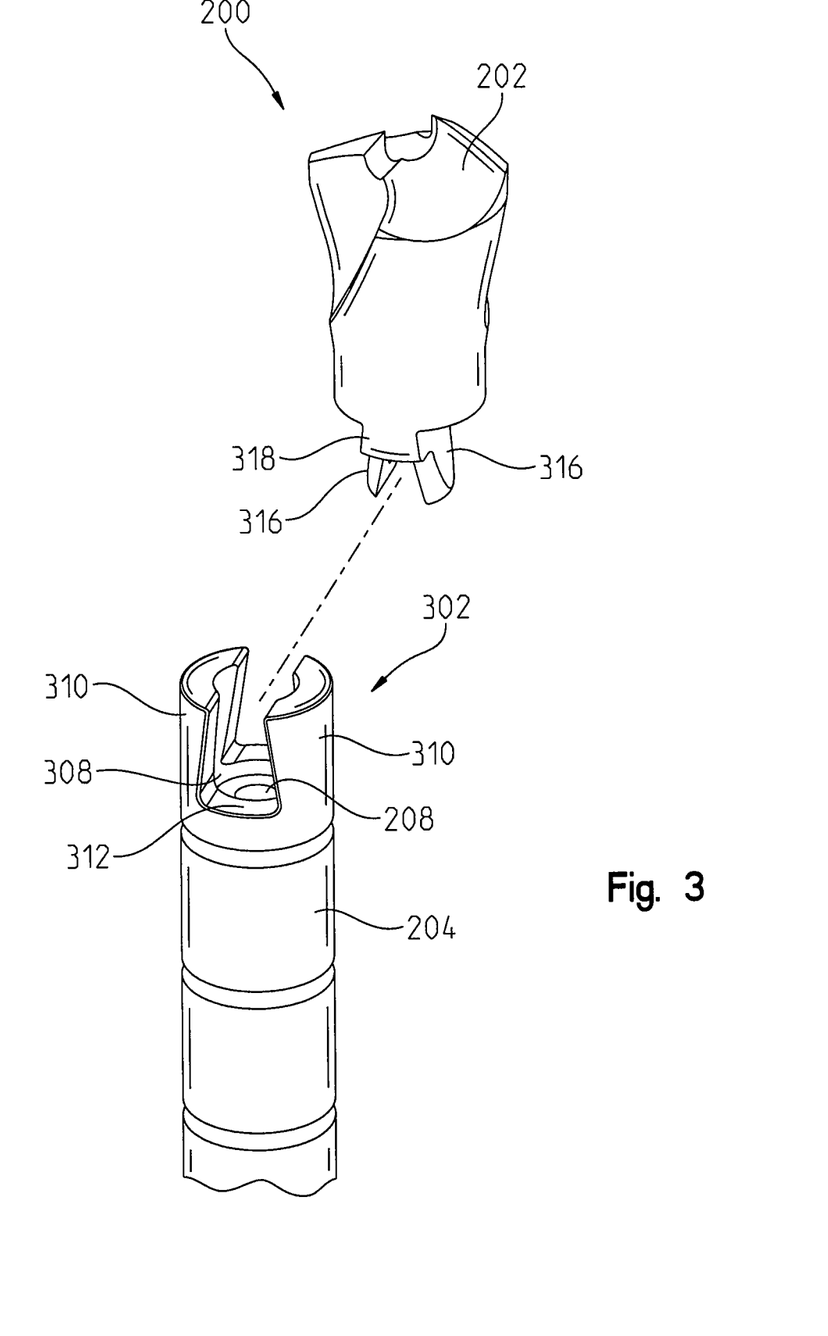
FIG. 3 represents a partial perspective view of the illustrative modular reamer drill tip connector assembly of FIG. 2 uncoupled from the reamer shaft.

To connect the cutting tip 202 to the reamer shaft 204 in accordance with the present teachings, multiple connection means are contemplated herein and may be utilized without straying from the intended scope of the present teachings. For instance, in accordance with one illustrative aspect of the present disclosure, and as is shown in FIGS. 3 and 4 in particular, the reamer shaft 204 may include a receiving end 302 that is configured to receive the cutting tip 202 during the assembly process. In accordance with this specific aspect of the present disclosure, the receiving end 302 defines a dovetail opening 308 that is comprised of a pair of outer walls 310 that extend upwardly from a base portion 312, which is in turn positioned adjacent to the proximal opening of the reamer shaft's through-hole 208. While the specific thickness of the outer walls 310 can be modified as desired, it should be understood and appreciated herein that the outer walls 310 should have a material thickness that is substantial enough to allow the reamer shaft 204 to maintain its structural integrity as it is being advanced through bone or tissue as part of a reaming procedure.

While not required herein, in accordance with certain aspects of the present disclosure, the receiving end 302 of the reamer shaft 204 may also include a counterbored hole 314 (FIG. 4) that is positioned along the center axis 210 of the reamer assembly. In accordance with this illustrative aspect of the present disclosure, the counterbored hole 314 can have a diameter that is greater than the reamer shaft's through-hole 208, yet less than the outer diameter of the reamer shaft 204.

To establish the removable connection between the cutting tip 202 and the reamer shaft 204, in accordance with certain aspects of the present disclosure, the cutting tip 202 comprises a pair of flexible arms 316 that are dimensioned to be received by the dovetail opening 308 of the reamer shaft's receiving end 302, and particularly such that they frictionally correspond with the outer walls 310 of the reamer shaft 204. In accordance with this embodiment, the flexible arms 316 are separated by a distance (as defined by the outside periphery of the flexible arms) that is slightly greater than the width of the dovetail opening 308 of the reamer shaft 204, yet positioned such that they still allow the cutting tip 202 to be slid into the dovetail opening 308 in a direction substantially transverse and perpendicular to the center axis 210 during the assembly process. More particularly, the flexible arms 316 can be dimensioned such that they can be sufficiently compressed as the cutting tip is slid into the dovetail opening 308 of the reamer shaft's receiving end 302. Further, as the cutting tip 202 becomes axially aligned with the reamer shaft 204, the flexible arms 316 can be at least partially decompressed as they enter part of the counterbored hole 314. As such, it should be understood and appreciated herein that the flexible arms 316 may act to at least partially hold the cutting tip 202 in axial alignment with the reamer shaft 204 once the cutting tip 202 is connected to the reamer shaft 204.

As shown in FIG. 3, the cutting tip 202 also includes a base portion 318 that is positioned and dimensioned to correspond with a portion of the dovetail opening 308 of the reamer shaft 204. In accordance with this aspect of the present disclosure, the base portion 318 is comprised of a substantially solid structure that is configured to serve as a means for transmitting the torsional load that is created when the assembly 200 is subjected to a rotary motion (i.e., a twisting or turning motion), as opposed to the torsional load being primarily transmitted through the flexible arms 316. More particularly, when the cutting tip 202 is axially centered with the reamer shaft 204, the dovetail opening 308 of the reamer shaft 204 is conformingly and structurally aligned with the base 318 such that when the assembly 200 is rotated, a substantial amount of the torsional load that is inherently created between the reamer shaft 204 and the cutting tip 202 will be distributed to the base portion 318 of the cutting tip 202, rather than primarily to the flexible arms 316.

Moving now to FIG. 4, a cutaway view of the reamer assembly 200 taken along line 4 of FIG. 2 is illustrated and structurally depicts the assembled relationship between the cutting tip 202 and the reamer shaft 204. Once assembled, the flexible arms 316 of the cutting tip 202 extend to and at least partially occupy the counterbored hole 314 and maintain the cutting tip 202 in axial alignment with the reamer shaft 204. Further, the base 318 also acts to keep the cutting tip 202 from detaching from the receiving end 302 of the reamer shaft 204 while maintaining a coaxial orientation. When the cutting tip 202 is coupled to the reamer shaft 204, it is substantially inhibited from sliding out of axial alignment with the reamer shaft because of the frictional engagement between the flexible arms 316 and the outer walls 310 of the reamer shaft 204, while simultaneously being inhibited from sliding away from the reamer shaft 204 because of the engagement between the base 318 and the dovetail opening 308 of the reamer shaft 204.

Figure 5:
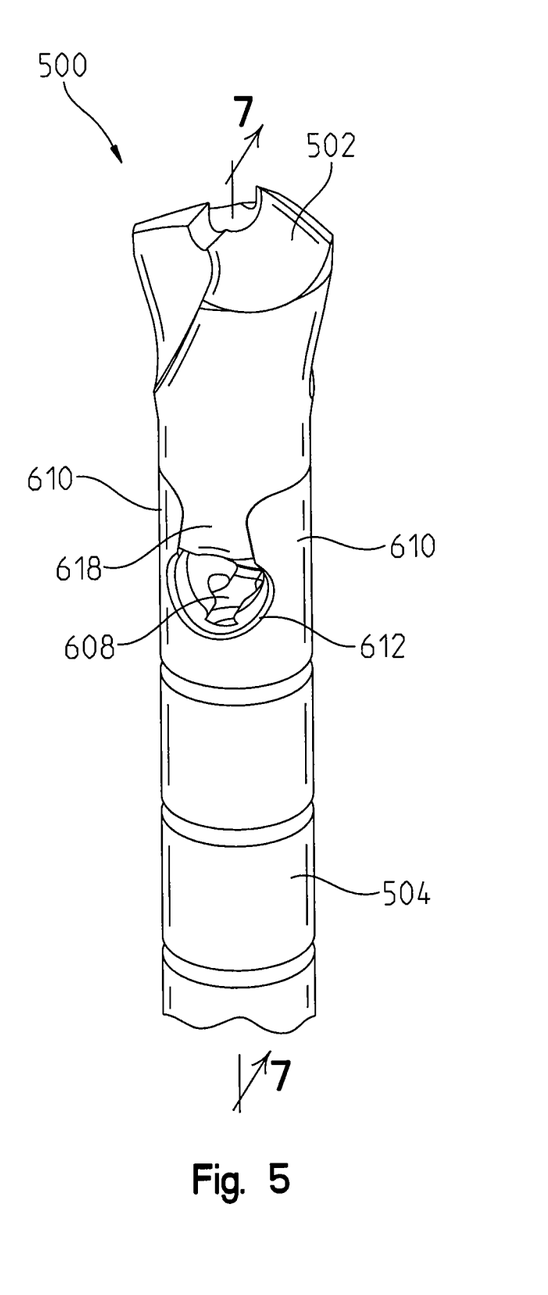
FIG. 5 represents a partial perspective view of another illustrative modular reamer drill tip connector assembly coupled to a reamer shaft in accordance with the teachings of the present disclosure.

FIGS. 5-8 illustrate another embodiment of the present disclosure, and particularly a reamer assembly 500 including a cutting tip 502 that is configured to be removably coupled to a reamer shaft 504 as part of a reaming procedure. As shown in FIG. 5 in particular, to advance the reamer assembly 500 over a guide wire, both the cutting tip 502 and the reamer shaft 504 include a through-hole along their respective center axes (i.e., through-hole 506 of the cutting tip 502 and through-hole 508 of the reamer shaft 504). As those of skill in the art will readily understand and appreciate herein, the releasable connection between the cutting tip 502 and the reamer shaft 504 can be configured such that through-holes 506 and 508 are capable of aligning with each other along the center axis 510 of the reamer assembly 500 such that a common through-hole that is adapted to receive the guide wire during a reaming process is created.

Figure 6:
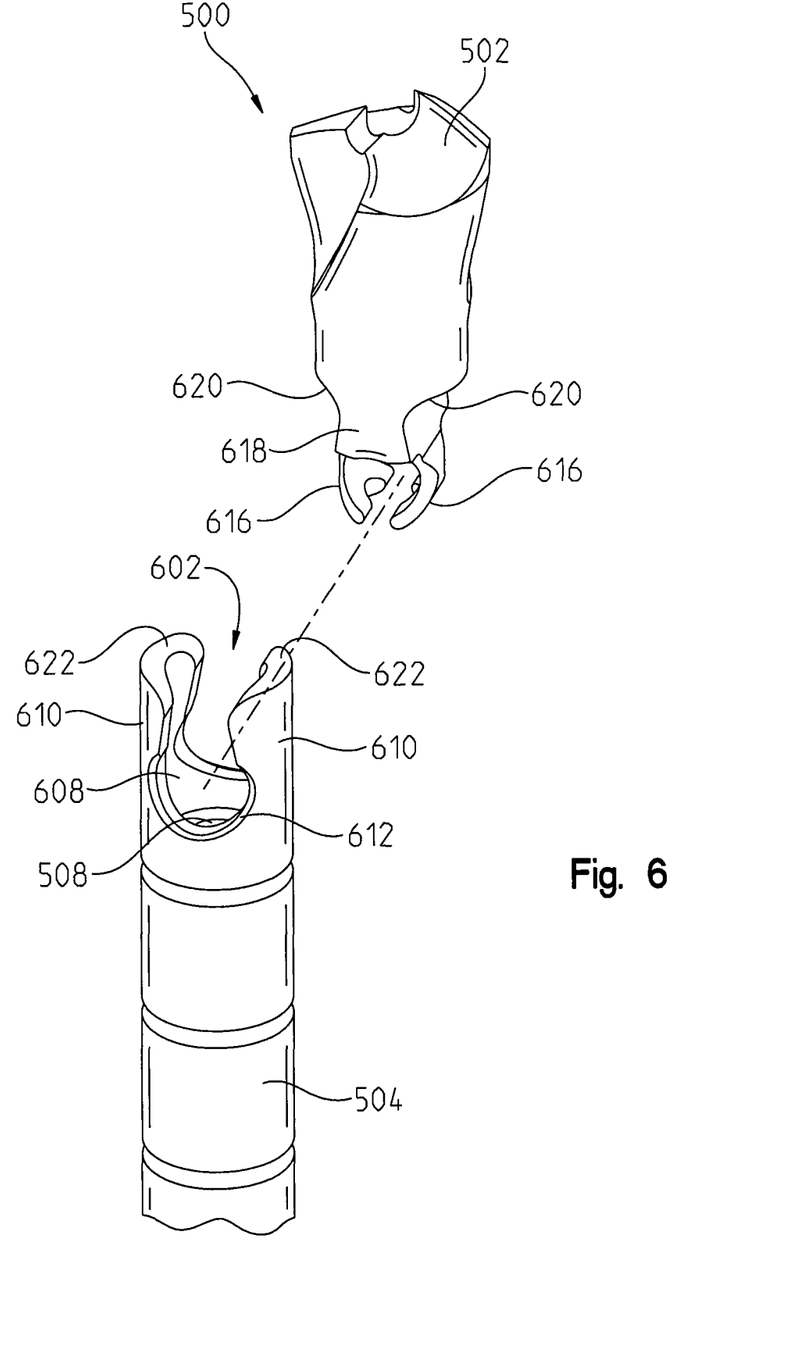
FIG. 6 represents a partial perspective view of the illustrative modular reamer drill tip connector assembly of FIG. 5 uncoupled from the reamer shaft.

To connect the cutting tip 502 to the reamer shaft 504 in accordance with this illustrative embodiment, the reamer shaft 504 includes a receiving end 602 that is configured to receive the cutting tip 502 during the assembly process. In accordance with this specific aspect of the present disclosure, the receiving end 602 defines a dovetail opening 608 that is comprised of a pair of outer walls 610 that extend upwardly from a curved base portion 612, which is in turn positioned adjacent to the proximal opening of the reamer shaft's through-hole 508. While the specific thickness and spacing of the outer walls 610 with respect to one another can be modified as desired, it should be understood and appreciated herein that the outer walls 610 should be positioned far enough from each other that the guide wire can be advanced through the through-hole 508 without encountering interference from the outer walls 610. In addition, the outer walls 610 should have a material thickness that is substantial enough to allow the reamer shaft 504 to maintain its structural integrity as it is being advanced through bone or tissue as part of a reaming procedure.

While not required herein, in accordance with certain aspects of the present disclosure, the receiving end 602 of the reamer shaft 504 may also include a counterbored hole 614 that is positioned along the center axis 510 of the reamer assembly. In accordance with this illustrative aspect of the present disclosure, the counterbored hole 614 can have a diameter that is greater than the reamer shaft's through-hole 508, yet less than the outer diameter of the reamer shaft 504.

To establish the removable connection between the cutting tip 502 and the reamer shaft 504, in accordance with certain aspects of the present disclosure, the cutting tip 502 comprises a pair of semicircular shaped flexible arms 616 that are dimensioned to be received by the dovetail opening 608 of the reamer shaft's receiving end 602, and particularly such that they frictionally correspond with the outer walls 610 of the reamer shaft 504. In accordance with this embodiment, the flexible arms 616 are separated by a distance that is slightly greater than the width of the dovetail opening 608 of the reamer shaft 504, yet positioned such that they still allow the cutting tip 502 to be slid into the dovetail opening 608 in a direction substantially transverse and perpendicular to the center axis 510 during the assembly process. More particularly, the flexible arms 616 can be dimensioned such that they can be sufficiently compressed as the cutting tip is slid into the dovetail opening 608 of the reamer shaft's receiving end 602. Further, as the cutting tip 502 becomes axially aligned with the reamer shaft 504, the flexible arms 616 can be at least partially decompressed as they enter part of the counterbored hole 614. As such, it should be understood and appreciated herein that the flexible arms 616 may act to at least partially hold the cutting tip 502 in axial alignment with the reamer shaft 504 once the cutting tip 502 is connected to the reamer shaft 504.

To further assist in the releasable connectivity between the cutting tip 502 and the reamer shaft 504 in accordance with the present teachings, the cutting tip 502 also includes a base portion 618 that is positioned and dimensioned to correspond with a portion of the dovetail opening 608 of the reamer shaft 504. In accordance with this aspect of the present disclosure, the base portion 618 is comprised of a substantially solid structure that is configured to serve as a means to transmit the torsional load that is created when the assembly 500 is subjected to a rotary motion, as opposed to the torsional load being primarily transmitted through the flexible arms 616. More particularly, when the cutting tip 502 is axially centered with the reamer shaft 504, the dovetail opening 608 of the reamer shaft 504 is conformingly and structurally aligned with the base 618 such that when the assembly 500 is rotated, a substantial amount of the torsional load that is inherently created between the reamer shaft 504 and the cutting tip 502 will be distributed to the base portion 618 of the cutting tip.

Figure 7:
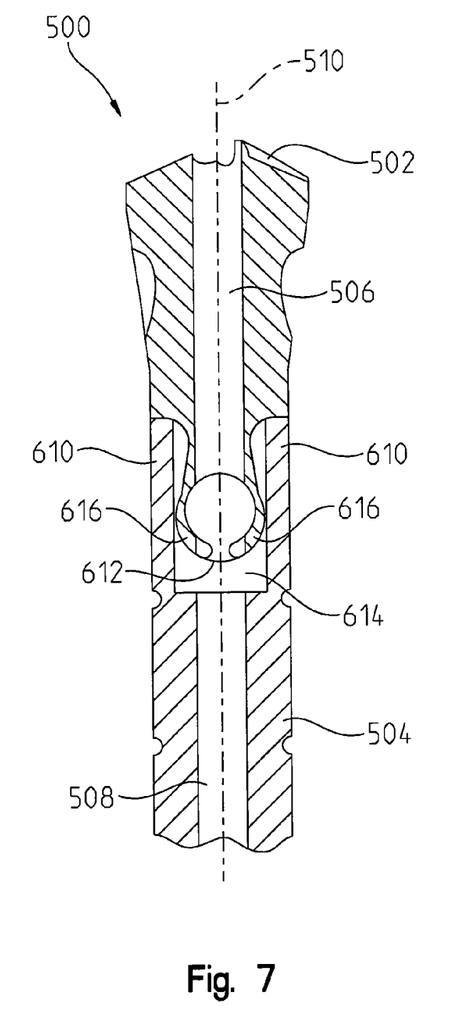
FIG. 7 represents a front, cross-sectional view of the illustrative modular reamer drill tip connector assembly coupled to the reamer shaft and taken along line 7 of FIG. 5.
Figure 8:
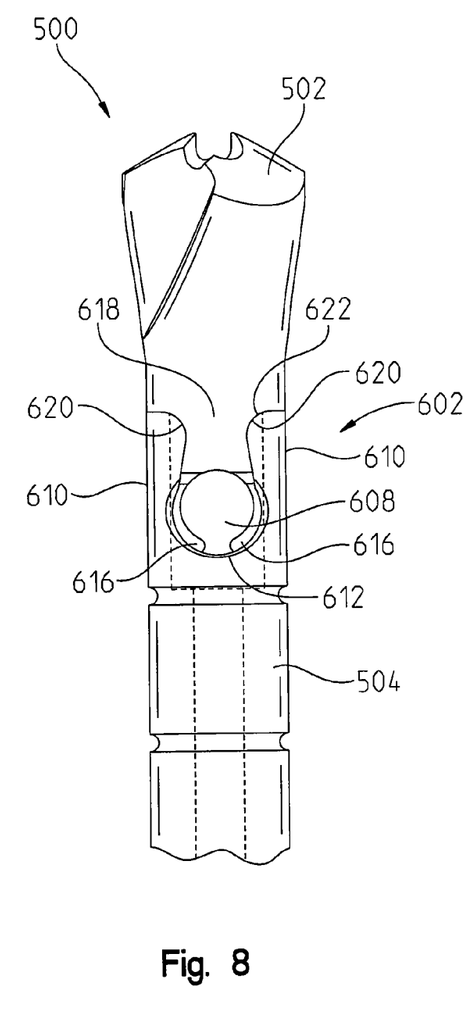
FIG. 8 represents a front, partial cross-sectional view of the illustrative modular reamer drill tip connector assembly of FIG. 5.

While those of skill in the art will understand and appreciate herein that the specific shape and configuration of the cutting tip 502 can be modified as desired, in accordance with certain aspects of the present disclosure, the base portion 618 of the cutting tip 502 may be tapered inwardly and include a rounded portion 620 that is configured to conformingly mate with a rounded top surface 622 of the flexible arms 610. In accordance with this aspect of the present disclosure, the engagement between the receiving end 602 of the reamer shaft 504 and the base 618 can be sufficient to adequately transmit torsional loads that are created when the reamer assembly 500 is subjected to rotary motion to the base portion 618 of the cutting tip 502. Moreover, and as is shown in FIGS. 7 and 8 in particular, the outer portion of the flexible arms 616 are configured such that they are capable of at least partially contacting the counterbored hole 614 once assembled. The contact between the flexible arms 616 and the counterbored hole 614, together with the contact between the receiving end 602 of the reamer shaft 504 and the base portion 618, ensures axial alignment and a frictional coupling between the cutting head 502 and the reamer shaft 504.

Figure 9:
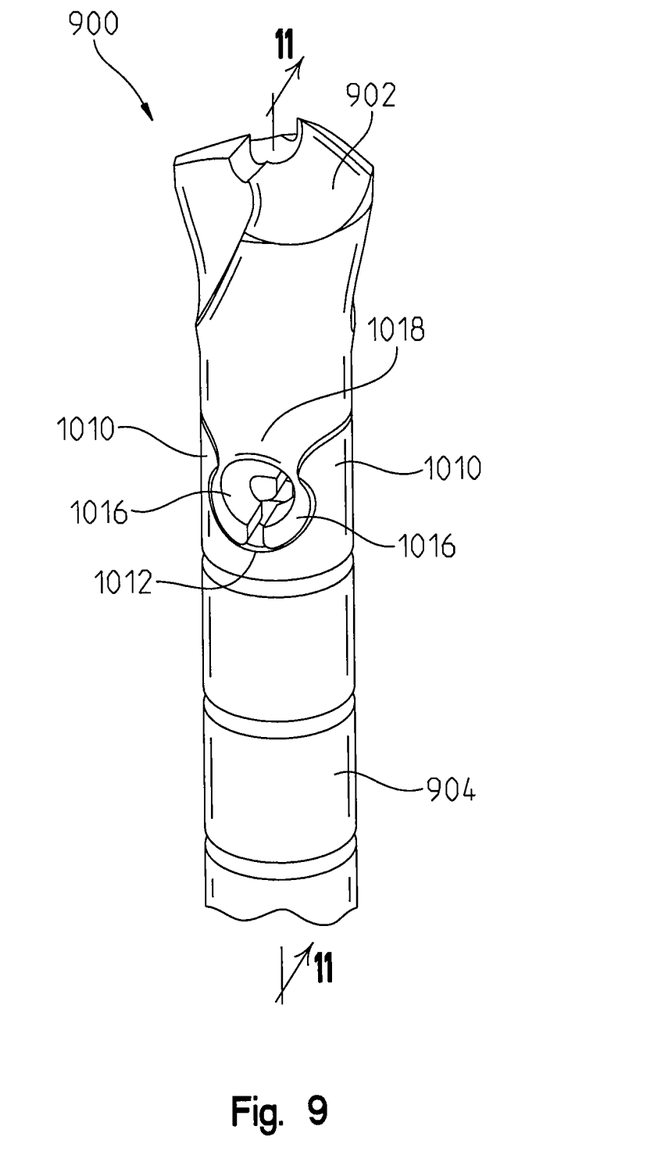
FIG. 9 represents a partial perspective view of yet another illustrative modular reamer drill tip connector assembly coupled to a reamer shaft in accordance with the teachings of the present disclosure.
Figure 10:
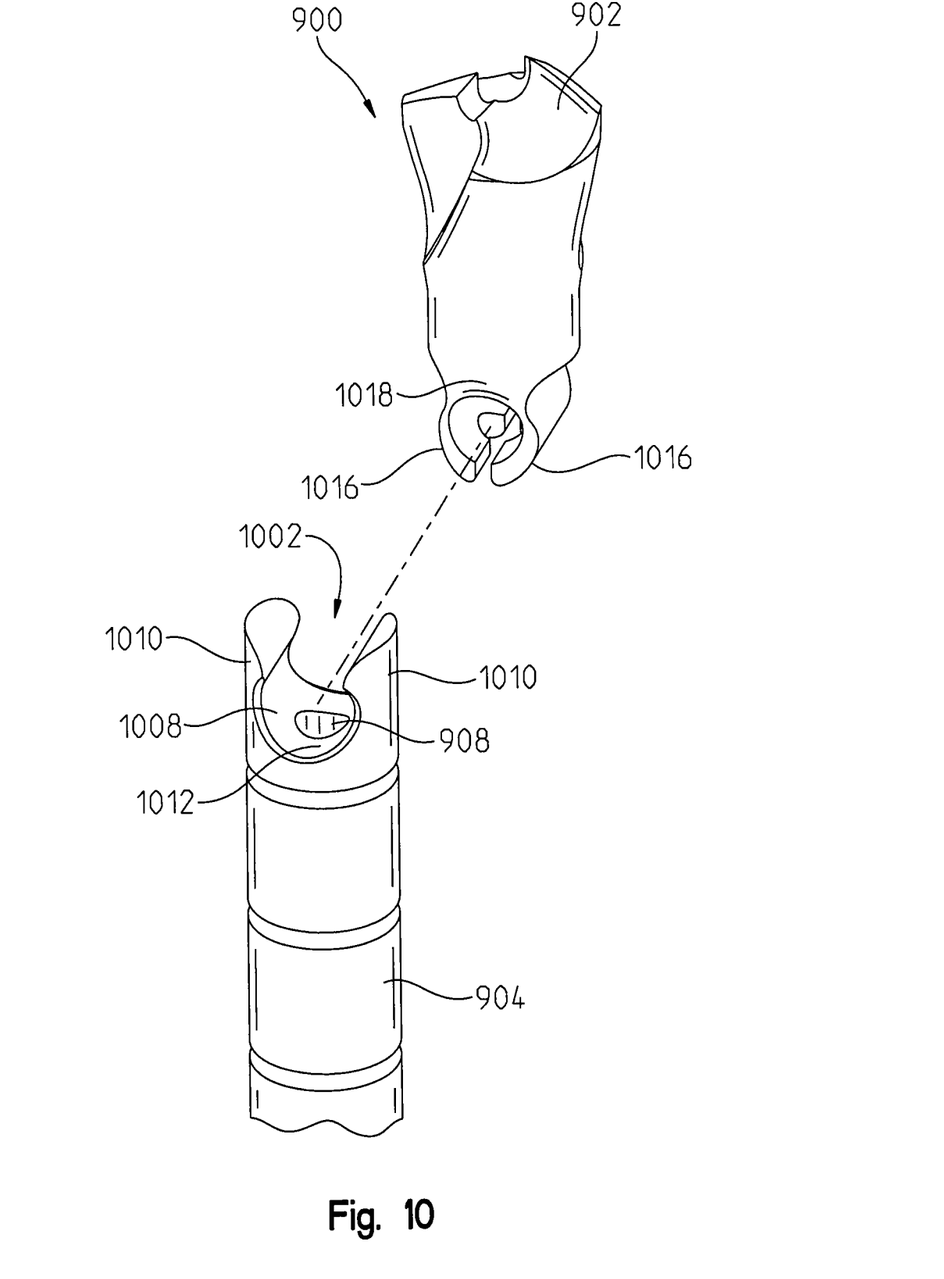
FIG. 10 represents a partial perspective view of the illustrative modular reamer drill tip connector assembly of FIG. 9 uncoupled from the reamer shaft.
Figure 11:
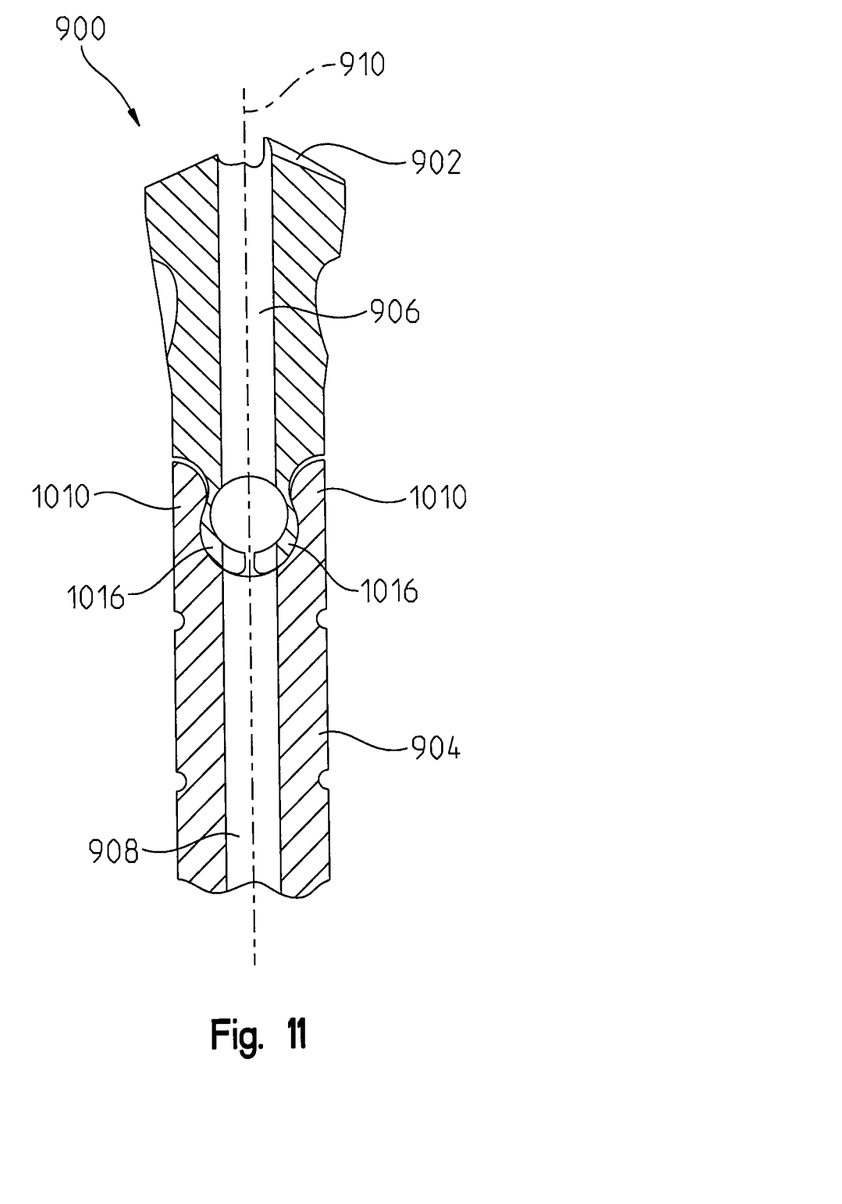
FIG. 11 represents a front, cross-sectional view of the illustrative modular reamer drill tip connector assembly coupled to the reamer shaft and taken along line 11 of FIG. 9.

Another illustrative reamer assembly 900 in accordance with the teachings of the present disclosure is shown in FIGS. 9-11. In particular, FIG. 9 depicts an illustrative reamer assembly 900 in accordance with an illustrative embodiment of the present disclosure. The reamer assembly 900 includes a cutting tip 902 that is configured to be removably coupled to a reamer shaft 904 as part of a reaming procedure. As shown in this embodiment, when the reamer shaft 904 and the cutting tip 902 are coupled to one another, the cutting tip 902 can be axially aligned with the reamer shaft 904 such that a torsional force from the reamer assembly 900 during a reaming procedure can be transmitted through the solid portion of the cutting tip 902. To advance the reamer assembly 900 over a guide wire, both the cutting tip 902 and the reamer shaft 904 include a through-hole along their respective center axes (i.e., through-hole 906 of the cutting tip 902 and through-hole 908 of the reamer shaft 904). As those of skill in the art will readily understand and appreciate herein, the releasable connection between the cutting tip 902 and the reamer shaft 904 can be configured such that through-holes 906 and 908 are capable of aligning with each other along the center axis 910 of the reamer assembly 900 such that a common through-hole that is adapted to receive the guide wire during a reaming process is created.

To connect the cutting tip 902 to the reamer shaft 904 in accordance with this illustrative embodiment, the reamer shaft 904 includes a receiving end 1002 that is configured to receive the cutting tip 902 during the assembly process. In accordance with this specific aspect of the present disclosure, the receiving end 1002 defines a dovetail opening 1008 that is comprised of a pair of outer walls 1010 that extend upwardly from a rounded base portion 1012, which is in turn positioned adjacent to the proximal opening of the reamer shaft's through-hole 908. While the specific thickness and spacing of the outer walls 1010 with respect to one another can be modified as desired, it should be understood and appreciated herein that the outer walls 1010 should be positioned far enough from each other that the guide wire can be advanced through the through-hole 908 without encountering interference from the outer walls 1010. In addition, the outer walls 1010 should have a material thickness that is substantial enough to allow the reamer shaft 904 to maintain its structural integrity as it is being advanced through bone or tissue as part of a reaming procedure.

To establish the removable connection between the cutting tip 902 and the reamer shaft 904, in accordance with certain aspects of the present disclosure, the cutting tip 902 comprises a pair of flexible arms 1016 that are dimensioned to be received by the dovetail opening 1008 of the reamer shaft's receiving end 1002, and particularly such that they frictionally correspond with the outer walls 1010 of the reamer shaft 904. In accordance with this embodiment, the flexible arms 1016 are separated by a distance that is slightly greater than the width of the dovetail opening 1008 of the reamer shaft 904, yet positioned such that they still allow the cutting tip 902 to be slid into the dovetail opening 908 in a direction substantially transverse and perpendicular to the center axis 910 during the assembly process. More particularly, the flexible arms 1016 can be dimensioned such that they can be sufficiently compressed as the cutting tip is slid into the dovetail opening 1008 of the reamer shaft's receiving end 1002.

The cutting tip 902 also includes a base portion 1018 that is positioned and dimensioned to correspond with a portion of the dovetail opening 1008 of the reamer shaft 904. In accordance with this aspect of the present disclosure, the base portion 1018 is comprised of a substantially solid structure that is configured to serve as a means to transmit the torsional load that is created when the assembly 900 is subjected to a rotary motion (i.e., a twisting or turning motion), as opposed to the torsional load being primarily transmitted through the flexible arms 1016. More particularly, when the cutting tip 902 is axially centered with the reamer shaft 904, the dovetail opening 1008 of the reamer shaft 904 is conformingly and structurally aligned with the base 1018 such that when the assembly 900 is rotated, a substantial amount of the torsional load that is inherently created between the reamer shaft 904 and the cutting tip 902 will be distributed to the base portion 1018 of the cutting tip.

Moving now to FIG. 11, a cutaway view of the reamer assembly 900 taken along line 11 of FIG. 9 is illustrated and structurally depicts the assembled relationship between the cutting tip 902 and the reamer shaft 904. Once assembled the flexible arms 1016 of the cutting tip 902 extend into and at least partially occupy the dovetail opening 1008 of the reamer shaft and maintain the cutting tip 902 in axial alignment with the reamer shaft 904. Further, the base 1018 also acts to keep the cutting tip 902 from detaching from the receiving end 1002 of the reamer shaft 904 while maintaining a coaxial orientation. When the cutting tip 902 is coupled to the reamer shaft 904, it is substantially inhibited from sliding out of axial alignment with the reamer shaft because of the frictional engagement between the flexible arms 1016 and the outer walls 1010 of the reamer shaft 904 while simultaneously being inhibited from sliding away from the reamer shaft 904 because of the engagement between the base 1018 and the dovetail opening 1008 of the reamer shaft 904.

One aspect of the present disclosure is the ability to removably couple a cutting tip to a reusable reamer shaft. The above embodiments illustrate and describe particular methods and designs for achieving such functionality but the disclosure should not be limited to such embodiments. One skilled in the art can realize how a plurality of design variations of the above embodiments could be used to achieve the described results. In addition, those of skill in the art will understand and appreciate herein that the various components (including the cutting tip and the reamer shaft) may be manufactured from a plurality of materials including, but not limited to, metal alloys, plastics, stainless steel, titanium, aluminum, brass, cobalt chrome molybdenum alloys, nitinol alloys, and the like, as well as various combinations thereof It should also be understood and appreciated herein that the cutting tip may include a plurality of flutes that aid in the removal of debris as the cutting tip reams bone and/or tissue during a reaming procedure. While those of skill in the art will understand and appreciate that the fluted portion may have various different shapes depending on the use of the cutting tip, in accordance with certain aspects of the present disclosure, the fluted portion may have a cylindrical or frustoconical shape. Moreover, it should also be understood and appreciated herein that the size, orientation and number of flutes defining the fluted portion can be adjusted as necessary without straying from the teachings of the present disclosure, and particularly depending on the intended application and use of the cutting tip.

One skilled in the art can appreciate how the present disclosure relates to allowing a cutting tip to be removably coupled to a shaft while simultaneously centering the cutting tip on the rotational axis of the shaft and providing sufficient structural integrity to adequately transfer the corresponding torsional loads that the cutting process may encounter. Finally, one skilled in the art could understand how the exact dimensions of the components of the receiving ends of both the shaft and the cutting tip could vary. The exact thickness of the outer walls of the shaft or the flexible arms can also vary as long as they correspond to provide the proper elastic properties to allow the cutting tip to be coupled to the shaft, and maintained in the appropriate orientation during use.

Those skilled in the art will also understand and appreciate herein that in addition to removably connecting the disclosed cutting tips with the reamer shafts by sliding the cutting tip into the opening of the reamer shaft in a direction substantially transverse and perpendicular to the central longitudinal axis of the shaft, the removable connection between the cutting tip and the reamer shaft may also be achieved by advancing the cutting tip into the dovetail opening in a direction co-axial with the center axis of the reamer shaft during the assembly process. In accordance with these envisioned embodiments, the flexible arms of the cutting tips can be dimensioned such that they can be sufficiently compressed (i.e., deflected inwardly) as the cutting tip is advanced downwardly into the dovetail opening of the reamer shaft's receiving end. More particularly, when the cutting tip is co-axially aligned with the reamer shaft, the cutting tip may be pressed into the reamer shaft. Once the cutting tip is partially inserted into the reamer shaft, the outer walls are slightly deflected in a radially outward direction as the flexible arms correspondingly deflect in a radially inward direction. To achieve such flexibility, those of skill in the art will understand and appreciated herein that both the outer walls and the flexible arms may be made from a sufficiently elastic material, as well as have a sufficient thickness to allow deflection during coupling, yet without causing permanent structural deformation. Moreover, it should be understood and appreciated herein that the elastic relationship between the outer walls and the flexible arms allows the cutting tip to be removed from the reamer shaft when subjected to an axially opposing force.

While an exemplary embodiment incorporating the principles of the present application has been disclosed hereinabove, the present application is not limited to the disclosed embodiments. Instead, this application is intended to cover any variations, uses, or adaptations of the application using its general principles. Further, this application is intended to cover such departures from the present disclosure as come within known or customary practice in the art to which this present application pertains and which fall within the limits of the appended claims.

The terminology used herein is for the purpose of describing particular illustrative embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations).

What is claimed is:

1. A reamer assembly comprising:
a modular drill tip having a cutting edge proximate a first end, a pair of flexible arms each including a planar surface extending from and proximate to a second end, the pair of flexible arms extending from the second end at a first flaring angle outward from a longitudinal axis such that a distal end of each flexible arms is s aced a first distance from the longitudinal axis and a proximal end of each flexible arms is spaced a second distance from the longitudinal axis, the first distance being greater than the second distance, and a first through-hole positioned between the first and second ends along the longitudinal axis, wherein the first through-hole is configured to receive a guide wire during a reaming process; and
a reamer shaft having a pair of outer walls each including a planar surface that extends from a base portion of the reamer shaft at a second flaring angle and a receiving end, the planar surfaces of the pair of outer walls contacting the planar surfaces of the pair of flexible arms when the modular drill tip is connected to the reamer shaft, the reamer shaft having a second through-hole that is configured to receive the guide wire during the reaming process, wherein the first and second through-holes together create a common through-hole that is positioned along the longitudinal axis.

2. The reamer assembly of claim 1, wherein the pair of outer walls that extend from the base portion of the reamer shaft extend from the base portion of the reamer shaft substantially adjacent to the second through-hole.

3. The reamer assembly of claim 1, wherein the receiving end further comprises a counterbored hole, the counterbored hole having a diameter that is greater than the diameter of the second through-hole, yet less than the diameter of the reamer shaft.

4. The reamer assembly of claim 1, wherein the pair of flexible arms is manufactured from an elastic material that is configured to be temporarily compressed in response to an external force.

5. The reamer assembly of claim 1, wherein the modular drill tip further includes a base portion that is configured to conformably engage the receiving end of the reamer shaft during assembly, wherein the engagement between the receiving end of the reamer shaft and the base portion is configured to transmit torsional loads that are created when the reamer assembly is subjected to rotary motion to the base portion of the drill tip.

6. A reamer assembly comprising:
a modular drill tip having a cutting edge proximate a first end and a pair of flexible arms, each of the flexible arms including a planar surface extending from a base portion that is positioned proximate to a second end, the pair of flexible arms extending from the base portion along a longitudinal axis such that a distal end of each flexible arm is spaced a greater distance from the longitudinal axis than a proximal end of each flexible arm, the base portion having a first planar surface, the modular drill tip also having a first throughhole positioned between the first and second ends along a longitudinal axis, wherein the first through-hole is configured to receive a guide wire during a reaming process; and
a reamer shaft having a receiving end that includes a second planar surface having a counterbored hole formed therein and that is configured to receive, and releasably engage in axial alignment thereto, the pair of flexible arms, the second planar surface in contact with the first planar surface when the reamer shaft is connected to the modular drill tip, the reamer shaft having a second through-hole that is configured to receive the guide wire during the reaming process, wherein the first and second through-holes together create a common throughhole that is positioned along the longitudinal axis; and
wherein the engagement between the pair of flexible arms and the counterbored hole is configured to transmit torsional loads that are created when the reamer assembly is subjected to rotary motion to the base portion of the modular drill tip,
wherein the receiving end of the reamer shaft includes a pair of outer walls, each of the outer walls including a planar surface that extends at a flaring angle from the receiving end and defining a dovetail opening configured to frictionally engage the planar surfaces of the flexible arms.

7. The reamer assembly of claim 6, wherein the dovetail opening is configured to receive the pair of flexible arms in a direction substantially transverse to the longitudinal axis.

8. The reamer assembly of claim 6, wherein the dovetail opening is configured to receive the pair of flexible arms in a direction substantially perpendicular to the longitudinal axis.

9. A modular drill tip for an orthopedic reamer comprising:
a cutting edge proximate a first end, the cutting edge being configured to penetrate a bony structure as the drill tip is imparted with rotary motion;
a pair of flexible arms, each of the flexible arms including a planar surface extending at a flaring angle from and proximate to a second end such that a distal end of each flexible arm is spaced a first distance from a longitudinal axis and a proximal end of each flexible arm is spaced a second distance from the longitudinal axis, the first distance being greater than the second distance, each of the planar surfaces having a conical shape arranged to frictionally engage complementary planar surfaces located at a receiving end of a reamer shaft; and a through-hole positioned between the first and second ends along a longitudinal axis, the through-hole being configured to receive a guide wire during a reaming process.

10. The modular drill tip of claim 9, wherein the pair of flexible arms is separated by a distance that is slightly greater than the width of the receiving end of the reamer shaft.

11. The modular drill tip of claim 9, wherein the pair of flexible arms is manufactured from an elastic material that is configured to be temporarily compressed in response to an external force.

12. The modular drill tip of claim 9, further including a base portion that is configured to conformably engage the receiving end of the reamer shaft during assembly, wherein the engagement between the receiving end of the reamer shaft and the base portion is configured to transmit torsional loads that are created when the drill tip is subjected to rotary motion to the base portion of the drill tip.

* * * * *

UNITED STATES PATENT AND TRADEMARK OFFICE
CERTIFICATE OF CORRECTION

PATENT NO. : 9,592,061 B2  
APPLICATION NO. : 14/019627  
DATED : March 14, 2017  
INVENTOR(S) : Norton et al.

Page 1 of 1

It is certified that error appears in the above-identified patent and that said Letters Patent is hereby corrected as shown below:

In the Claims

In Column 11, Line 35, in Claim 1, delete "s aced", insert --spaced-- therefor In Column 11, Line 38, in Claim 1, before "axis,", insert --axis and a proximal end of each flexible arms is spaced a second distance from the longitudinal-- therefor In Column 12, Line 20, in Claim 6, delete "throughhole" and insert --through-hole-- therefor In Column 12, Line 35, in Claim 6, delete "throughhole" and insert --through-hole-- therefor Signed and Sealed this  
Twelfth Day of June, 2018

Andrei Iancu  
*Director of the United States Patent and Trademark Office*